US00PP28891P2

(12) United States Plant Patent
Podaras

(10) Patent No.: US PP28,891 P2
(45) Date of Patent: Jan. 23, 2018

(54) ***BUDDLEIA* PLANT NAMED 'PPODARAS25'**

(50) Latin Name: ***Buddleia* hybrid**
Varietal Denomination: PPODARAS25

(71) Applicant: Peter Podaras, Salem, OR (US)

(72) Inventor: Peter Podaras, Salem, OR (US)

( * ) Notice: Subject to any disclaimer, the term of this patent is extended or adjusted under 35 U.S.C. 154(b) by 0 days.

(21) Appl. No.: 15/330,505

(22) Filed: Sep. 29, 2016

(51) Int. Cl.
*A01H 5/00* (2006.01)

(52) U.S. Cl.
USPC ..... Plt./242

(58) Field of Classification Search
USPC ..... Plt./242
CPC ..... A01H 5/00; A01H 5/02
See application file for complete search history.

*Primary Examiner* — Kent L Bell
(74) *Attorney, Agent, or Firm* — Penny J. Aguirre

(57) ABSTRACT

A new cultivar of *Buddleia* plant named 'PPODARAS25', that is characterized by its inflorescences with individual flowers that are large in size, its flowers that are bright violet-blue in color, its compact and densely branched plant habit; its growth habit with no dominance leader, and its ability to bloom as a young plant.

2 Drawing Sheets

Botanical classification: *Buddleia* hybrid.
Variety denomination: 'PPODARAS25'.

BACKGROUND OF THE INVENTION

The present invention relates to a new and distinct cultivar of *Buddleia* hybrid and will be referred to hereafter by its cultivar name, 'PPODARAS25'. 'PPODARAS25' is a new shrub grown for use as an ornamental landscape plant.

The new cultivar of *Buddleia* is a selection from an ongoing breeding program conducted by the Inventor in Davis, Calif. with the objective of creating new cultivars of *Buddleia* with more floriferous blooming habits, compact plant habits, and larger individual flowers with brighter colors.

The new variety of *Buddleia*, 'PPODARAS25', arose from a cross made in 2014 between an unnamed and unpatented proprietary plant of *Buddleia* from the Inventor's breeding program as the female parent and pollen that was pooled from a variety of unnamed and unpatented plants from his breeding program as the male parent. 'PPODARAS25' was selected from amongst the resulting seedlings as a single unique plant in 2016.

Asexual propagation of the new cultivar was first accomplished by the Inventor using stem cuttings in 2015 in Silverton, Oreg. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PPODARAS25' as a unique cultivar of *Buddleia*.

1. 'PPODARAS25' exhibits inflorescences with individual flowers that are large in size.
2. 'PPODARAS25' exhibits flowers that are bright violet-blue in color.

3. 'PPODARAS25' exhibits a compact and densely branched plant habit.
4. 'PPODARAS25' exhibits a growth habit with no dominance leader.
5. 'PPODARAS25' exhibits blooms as a young plant in a 4-inch container.

The female parent differs from 'PPODARAS25' in having flowers that are smaller in size and deep red in color and in having a less vigorous growth habit.

'PPODARAS25' can be compared to the *Buddleia* cultivars 'Black Knight' (not patented) and 'Blue Chip' (U.S. Plant Pat. No. 19,991). 'Black Knight' is similar to 'PPODARAS25' in flower color. 'Black Knight' differs from 'PPODARAS25' in having a larger plant size and habit. 'Blue Chip' is similar to 'PPODARAS25' in having a compact plant habit. 'Blue Chip' differs from 'PPODARAS25' in having inflorescences and flowers that are smaller in size and flowers that are more blue in color.

BRIEF DESCRIPTION OF THE DRAWINGS

The accompanying photographs illustrate the characteristics of a 1 year-old plant as grown in Silverton, Oreg.

The photograph in FIG. 1 provides a view of a plant of 'PPODARAS25' in bloom.

Figure 1:
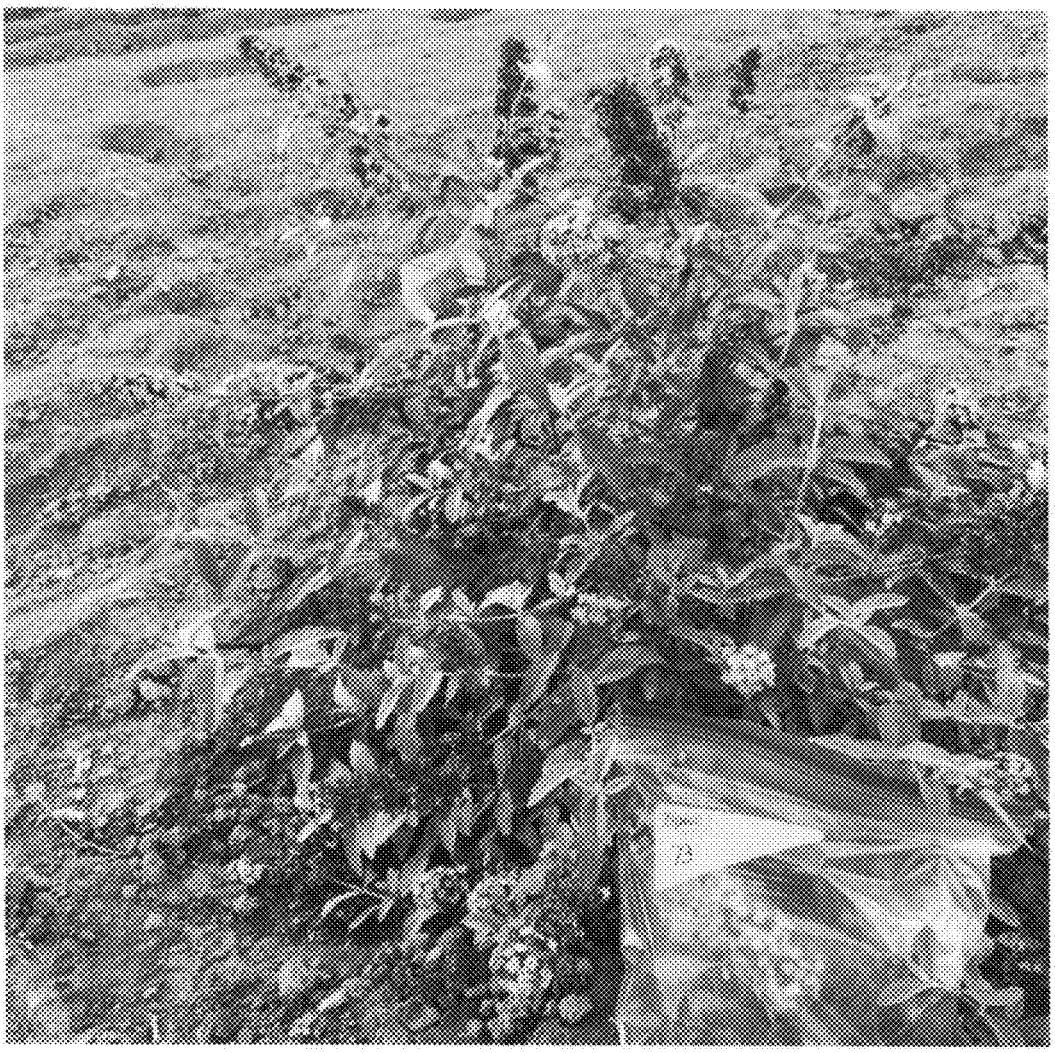
Figure 2:
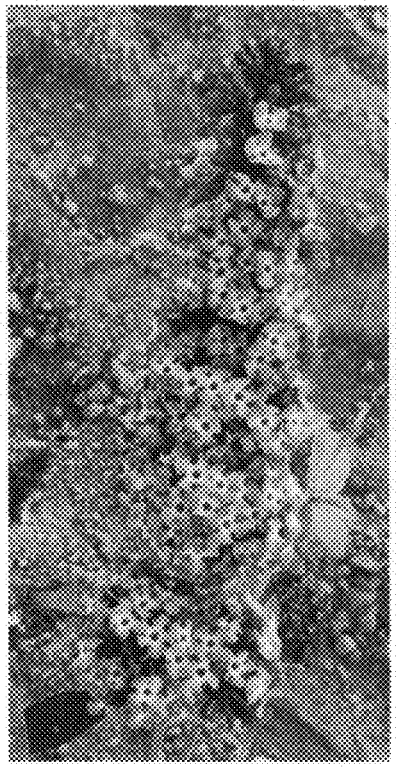

The photograph in FIG. 2 provides a close-up view of an inflorescence of 'PPODARAS25'.

Figure 3:
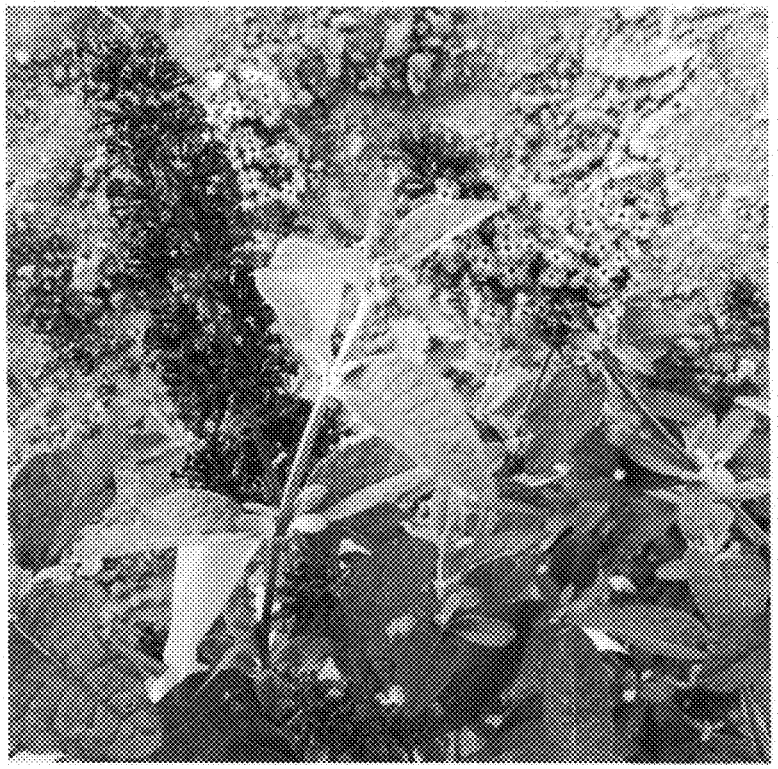

The photograph in FIG. 3 provides a close-up view of a branch of 'PPODARAS25'.

The colors in the photograph may differ slightly from the color values cited in the detailed botanical description, which accurately describe the colors of the new *Buddleia*.

DETAILED BOTANICAL DESCRIPTION

The following is a detailed description of 1 year-old plants of the new cultivar as field grown outdoors in Silverton, Oreg. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period.*—Late spring to early summer through fall in Oregon until temperatures fall below 18.3° C.

*Plant type.*—Deciduous shrub.

*Plant habit.*—Rounded, compact, densely branching and wider than it is tall.

*Plant size.*—An average of 1.7 m in height and 2 to 3 m in width for a mature plant when cut back to the soil level in spring.

*Hardiness.*—At least to U.S.D.A. Zones 8 to 10.

*Diseases and pests.*—No susceptibility and resistance to diseases and pests has been observed.

*Root description.*—Fibrous and fine, 155D in color.

*Propagation.*—Stem cuttings.

*Time required for root development.*—Roots initiate in an average of 14 days, a fully rooted plant in a 1.38-L container is produced in 10 to 12 weeks.

*Growth rate.*—Good vigor with a moderate growth rate.

Branch description:

*Branch shape.*—Square, with raised corners down the length of the stem.

*Branch color.*—148B on lower branch region without sun exposure (143C with flocci rubbed off) and 200B on sun exposed areas (N79B with flocci rubbed off).

*Branch strength.*—Strong and very flexible.

*Branch size.*—15 to 22 cm in length and an average of 3 mm in diameter (mid point).

*Branch surface.*—Smooth and dense covered with tangled floccose hairs.

*Branching.*—500 to 700 lateral branches per 167.64 cm plant.

*Internode length.*—5 to 10 cm.

Foliage description:

*Leaf shape.*—Elliptic.

*Leaf division.*—Simple.

*Leaf base.*—Attenuate and very minutely oblique (1 mm).

*Leaf apex.*—Obtuse.

*Leaf fragrance.*—None.

*Leaf venation.*—Brochidodromous with tertiary veins, color; upper surface 11D, lower surface 194C.

*Leaf margins.*—Serrulate.

*Leaf arrangement.*—Nearly opposite (each pair of leaves is turned about 15° from previous pair).

*Leaf attachment.*—Petiolate.

*Leaf surface.*—Upper surface; papillate with stellate hairs and impressed veins and occasional glandular bodies, lower surface; highly flocculent with stellate hairs and raised veins.

*Leaf size.*—6 to 8 cm in length and 2.5 to 4 cm in width.

*Leaf quantity.*—An average of 8 to 10 per branch.

*Leaf color.*—Young and mature upper surface; 138C (with flocci rubbed off 139A), young lower surface; 191D, mature lower surface; 191B.

*Petioles.*—2 to 3 mm in length and 1 to 2 mm in diameter, 194C in color with surface exposed to direct sun light N79C in color on outer edges, flocculent surface.

Inflorescence description:

*Inflorescence type.*—Compound terminal panicles roughly conical in shape.

*Inflorescence size.*—12 to 16 cm in height and an average of 5 cm in diameter at the widest point.

*Lastingness of flowers.*—An average of 9 to 12 days.

*Flower buds.*—Conical in shape, an average of 1 mm in depth and 5 mm in diameter, 200A in color.

*Flower aspect.*—Outward and upright.

*Flower fragrance.*—Strong and sweet.

*Flower quantity.*—Up to 1,200 flowers per inflorescence.

*Flower type.*—Single and salverform.

*Flower size.*—Up to 5.5 cm in diameter and an average of 4.5 cm in depth.

*Peduncles.*—1.7 to 6 cm in length and 1.5 to 3.5 mm in diameter, 148B in color (143C with flocci rubbed off), moderately strong and flexible, surface is smooth with dense tangled floccose hairs.

*Pedicels.*—0.5 to 2 mm in length and 1 mm in diameter, 194A in color, moderately strong and very flexible, surface covered with floccose hairs.

*Calyx.*—Tetragonal in shape.

*Sepals.*—4, occasionally 5, ovate and fused into a campanulate overall shape, margins mainly entire, dentate near the base, acute apex with anthocyanin tip, lower ½ to ⅔ fused at base, and average of 4 mm in length and 2 mm in width, color; upper surface when opening and when fully open; N138B with 200B at the tip, lower surface when opening and when fully open 138B, upper surface floccose, lower surface glandular.

*Petals.*—4 to 5, arrangement in a single whorl and fused into narrow tube, flabellate in shape, crenate margin, obtuse apex, an average of 1.4 cm in length and 5 mm in width, upper and lower surface is papillate and undulate with stellate hairs at base, color; upper surface when opening 96C, 97C towards the center, N25C at the very base and into the corolla tube, lower surface when opening 96A, upper surface when fully open 94B transitioning near margin to 97B and to N25C at the very base and into the corolla tube, lower surface when fully open 94A.

Reproductive organs:

*Gynoecium.*—1 pistil, an average of 4.25 mm in length, stigma; oblong in shape, retuse apex, fused into 2 parts, 148A in color, style; an average of 1 mm in length, square in shape, and 145B in color, ovary; hypogynous and 139C in color.

*Androecium.*—Stamens; 4, rarely 5, filament; fused directly to the base, 161A and 165A in color, anthers; 1.25 mm in length, 161A and 165A in color, pollen; none produced.

*Fruit and seed.*—Have not been produced to date.

It is claimed:

1. A new and distinct cultivar of *Buddleia* plant named 'PPODARAS25' as herein illustrated and described.

* * * * *